(12) United States Patent
Smith et al.

(10) Patent No.: US 6,408,981 B1
(45) Date of Patent: Jun. 25, 2002

(54) EXTRUDED MONOLITHIC FOAM EARPLUG

(75) Inventors: James C. Smith, Granville; Gary L. Wood, North Granville, both of NY (US)

(73) Assignee: Saint-Gobain Performance Plastics Corporation, Wayne, NJ (US)

( * ) Notice: Subject to any disclaimer, the term of this patent is extended or adjusted under 35 U.S.C. 154(b) by 0 days.

(21) Appl. No.: 09/670,678

(22) Filed: Sep. 27, 2000

(51) Int. Cl.7 .................................................. A61B 7/02
(52) U.S. Cl. ........................................ 181/315; 181/128
(58) Field of Search ................................ 181/128, 129, 181/135, 134; 128/864

(56) References Cited

U.S. PATENT DOCUMENTS

| | | | |
|---|---|---|---|
| 3,811,437 A | | 5/1974 | Gardner, Jr. |
| RE29,487 E | | 12/1977 | Gardner, Jr. |
| 4,160,449 A | | 7/1979 | Wade |
| 4,702,238 A | | 10/1987 | Scott |
| 4,774,938 A | | 10/1988 | Leight |
| 4,852,684 A | * | 8/1989 | Packard .................... 181/131 |
| 5,044,463 A | | 9/1991 | Carr |
| 5,119,833 A | | 6/1992 | Powers |
| 5,203,352 A | | 4/1993 | Gardner, Jr. |
| 5,207,827 A | | 5/1993 | Tokarz |
| 5,298,692 A | * | 3/1994 | Ikeda et al. .................... 181/135 |
| D371,193 S | | 6/1996 | Myers et al. |
| 5,572,594 A | * | 11/1996 | Devoe et al. ................ 381/68.6 |
| 5,573,015 A | * | 11/1996 | Willaims .................... 128/864 |
| 5,718,244 A | * | 2/1998 | Thornton .................... 128/864 |
| 5,792,998 A | | 8/1998 | Gardner, Jr. et al. |
| 5,811,742 A | * | 9/1998 | Leight ........................ 181/135 |
| 5,904,143 A | | 5/1999 | Magidson |
| 5,988,313 A | * | 11/1999 | Hakansson .................. 181/135 |

FOREIGN PATENT DOCUMENTS

DE 2500534 7/1976

OTHER PUBLICATIONS

NTP 67 SAF Compressions test (method C) Published by Norton Performance Plactics Corporation 1996.
NTP 102 SAF Recovery Test Published by Norton Performance Plactics Corporation 1996.

* cited by examiner

Primary Examiner—Robert E. Nappi
Assistant Examiner—Kim Lockett
(74) Attorney, Agent, or Firm—Volker R. Ulrich, Esq.; Sampson & Associates, P.C.

(57) ABSTRACT

A monolithic earplug being compressible or deformable. The earplug is fabricated from an extruded, elastomeric thermoplastic in order that it may be rapidly and efficiently produced, and then the extrudate is cut at the die face, as it emerges therefrom, into discrete pieces to form earplugs having convex end portions and a skin extending over its entire outer surface.

26 Claims, 4 Drawing Sheets

EXTRUDED MONOLITHIC FOAM EARPLUG

BACKGROUND OF THE INVENTION

1. Technical Field

This invention relates to extruded earplugs for dampening airborne sound, and a method for producing such earplugs.

2. Background Information

Earplugs designed to be inserted into a person's ear canals to dampen sound and prevent the entry of foreign matter are known in the art. Historically, these earplugs were manufactured from fibrous materials such as cotton. In more recent times, earplugs have been produced from polymer based materials, which tend to be more durable than the fibrous materials formerly used. One conventional method for making polymer-based earplugs is by die cutting plugs from sheets of cellular material such as vinyl or polyurethane foam. Such die cut plugs are usually cylindrically shaped in order that the earplugs can readily conform to the shape of a human ear canal. As a result, the amount of material waste in die cut plug production tends to be great (i.e., on the order of ½ of the foam web material) because the web between cut cylindrical earplugs cannot be used. The material used is often not recyclable, therefore, disposal of the waste material can represent a significant manufacturing expense. In addition, earplugs produced by this method have cut cells along their cylindrical surfaces. As a result, they have a rough surface which can be uncomfortable to the wearer and harbor dirt. These earplugs can also be difficult to insert into a wearer's ear canals because they tend to lack longitudinal rigidity.

Another method for producing polymer-based earplugs is by molding them to the desired shape. For example, U.S. Pat. Nos. 4,774,938 and 3,872,559, both to Leight, disclose earplugs molded from polymer-based materials. Molded earplugs can be manufactured so that they are specially shaped and covered by a protective skin, enhancing their comfort and fit. However, the process of molding earplugs tends to be slower and more capital intensive than die cutting due to the large number of molds required. In addition, molded earplugs may be relatively difficult to insert into a user's ears due to the fact that the polymer materials from which they are manufactured tend to lack longitudinal rigidity.

Attempts have been made to provide earplugs having sufficient longitudinal rigidity to allow them to be easily inserted into the ears and sufficient compressibility to allow snug yet comfortable wearer fit. For example, multi-component earplugs having a compressible element and a more rigid element are taught by U.S. Pat. No. 5,188,123 to Gardner, and U.S. Pat. No. 4,434,794 to Leight. Because the rigid and compressible elements of those earplugs must be individually manufactured and then joined together, their production processes tend to be slower and more costly than those for die cut earplugs.

U.S. Pat. No. 5,573,015 to Williams attempts to overcome some of the aforementioned drawbacks through the provision of a composite extruded earplug having a relatively soft sheath component surrounding a relatively rigid core component. The core component is provided to improve the longitudinal stiffness of the earplug, while the sheath component provides resiliency and user comfort. The composite aspect of this device, however, tends to disadvantageously complicate and/or increase the cost of the earplug. The thermoplastic elastomer of Williams' device also tends to be disadvantageously expensive. In addition, the relatively stiff core may impinge on a user's ear canal during insertion to cause user discomfort. Such a device also may be difficult to sufficiently compress for easy insertion into the user's ear canal.

Thus, a need exists for a readily manufacturable and inexpensive sound dampening earplug providing the requisite compressibility for easy ear insertion, along with comfortable fit.

SUMMARY

According to the present invention, a method is provided for fabricating an earplug. The method includes using an extruder having a die to extrude a monolithic body of foamed elastomeric thermoplastic material about 10 to 20 millimeters in diameter. The extrudate is then cut into discrete pieces about 10–35 millimeters in length to form individual earplugs.

In another aspect of the invention, an earplug sized and shaped for being received in the human ear canal is provided. The earplug includes an extruded monolithic body of foamed elastomeric thermoplastic material about 10 to 20 millimeters in diameter having a length of about 10–35 millimeters.

A further aspect of the present invention includes a monolithic earplug formed by the process of disposing a PVC-based material within an extruder under heat and pressure and incorporating a blowing agent into the material. The material is then extruded in a longitudinal direction from a die into an ambient environment wherein the blowing agent foams the extrudate, the extrudate having a transverse cross-sectional dimension of about 10 to 20 millimeters. The extrudate is cut at a 90 degree angle to the longitudinal direction, as it emerges from the die, prior to substantially complete cooling and expansion thereof. A convex, skinned surface is then formed at the cut ends as the extrudate subsequently expands and cools to form a monolithic earplug. The earplug has a density of about 6 to 12 pcf (96 to 192 kg/m$^3$) and a rate of recovery from 80 percent compression sufficient to recover about 90 percent or less of its initial transverse cross-sectional dimension in 45 seconds, and after being compressed under a 5 pound weight for 6 seconds, to recover about 90 percent or more of its initial transverse cross-sectional dimension in 90 seconds. The use of such inherently-formed convex surfaces tends to aid insertion of the earplugs, without requiring any additional shaping operations. Provision of a skin on the ends, as well as the sides, of the earplugs advantageously tends to enhance the ability of the plug to block sound and improves the cleanliness due to the substantial elimination of open cells.

The monolithic structure forming the earplug is preferably capable of being compressed or deformed by hand down to about 20–50% or less of its original diameter. The slow recovery from compression facilitates ear insertion, while the tendency to return to its original dimensions advantageously serves to achieve a snug fit within the wearer's ear.

BRIEF DESCRIPTION OF THE DRAWINGS

The above and other features and advantages of this invention will be more readily apparent from a reading of the following detailed description of various aspects of the invention taken in conjunction with the accompanying drawings, in which.

DETAILED DESCRIPTION

Figure 1:
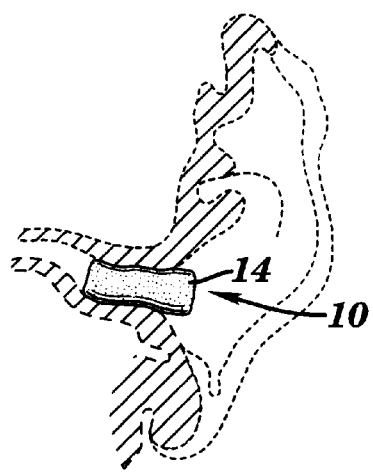
FIG. 1 is a sectional environmental view of an earplug according to the present invention inserted in a wearer's ear.
Figure 2:
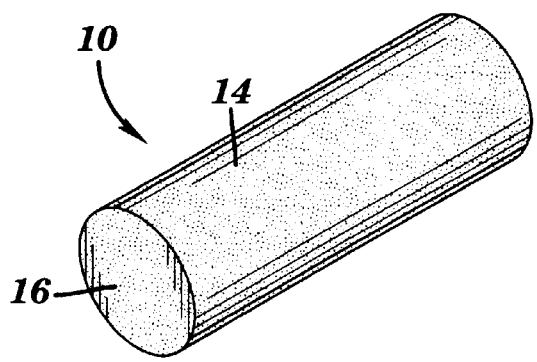
FIG. 2 is a perspective view of an earplug according to an embodiment of the present invention having squared-off, planar end portions.
Figure 3:
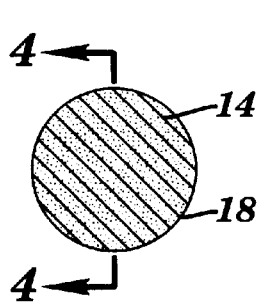
FIG. 3 is a cross-sectional view of the earplug shown in FIGS. 2 and 4, as shown along line 3—3 of FIG. 4.
Figure 4:
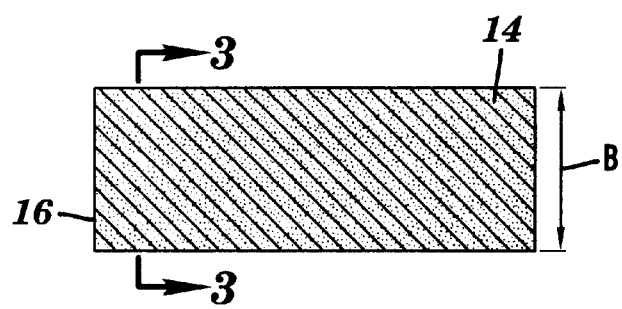
FIG. 4 is a longitudinal cross-sectional view taken along line 4—4 of FIG. 3.

Referring to the figures set forth in the accompanying Drawings, the illustrative embodiments of the present invention will be described in detail herein below. For clarity of exposition, like features shown in the accompanying Drawings shall be indicated with like reference numerals and similar features as shown in alternate embodiments in the Drawings shall be indicated with similar reference numerals.

Referring now to FIGS. 1–7, the present invention is directed to an earplug 10 designed to be inserted in a human ear canal for dampening airborne sound and protecting against the entry of foreign matter into the ear canal. The earplug 10 of the present invention comprises a monolithic body 14. The body 14 is sufficiently soft and flexible to provide a comfortable fit for the wearer. The earplug 10 is desirably compressible or deformable in order that it can be compressed and inserted into a wearer's ear canal. The earplug 10 also preferably includes an outer skin 18 (FIG. 3) that provides sufficient longitudinal rigidity to facilitate such insertion. The earplugs of the present invention advantageously generate less manufacturing waste than prior art foam casting and die cutting processes. The present invention is also simpler to manufacture and more comfortable to the user than prior art composite ear plugs. Moreover, the extruded earplugs provide the unexpected benefit of greater sound attenuation than earplugs of the prior art.

As shown, the body 14 preferably has a consistent cross-sectional diameter B. The body 14 is preferably made from a compressible or deformable material such as a low density thermoplastic polymer material. The material may be a solid or a cellular material. The material desirably has a slow recovery from compression or deformation. Particularly preferred are materials that recover substantially all of their initial volume at a relatively slow rate of recovery. For example, such suitable materials preferably have a rate of recovery sufficient to recover 90 percent or less of their initial volume within 40–45 seconds. These materials should also recover about 90 percent or more of their initial volume within about 90 seconds. These parameters are set forth in greater detail in NTP 67 SAF Compression Test and NTP 102 SAF Recovery Test, published in 1996 by Norton Performance Plastics Corporation, and which are fully incorporated by reference herein.

In addition to the foregoing rate of recovery parameters, in order that the earplug 10 can conform to the shape of a wearer's ear canal, it is preferable that the body material provides a structure that is compressible by hand to down to about 40 to 50% or less of its original diameter.

Preferred materials for forming the body 14 are low density thermoplastic materials such as PVC. Alternate materials that may be useful include thermoplastic elastomers such as thermoplastic Polyolefins/ethylene-propylene (PEP OR EPDM), thermoplastic block copolymers/styrene-butadiene (SBS) and styrene-isoprene (SIS), thermoplastic polyester, thermoplastic polyurethane (PU)/polyester/polyether, thermoplastic vulcanizates, melt processible rubbers, polyamide blocks, thermoplastic rubber, and viscoelastic polyurethane. Santoprene® thermoplastic rubber sold by Advanced Elastomer Systems may also be used. The material selected has a density sufficient to produce earplugs having densities ranging from about 2 to 20 pcf (32 to 320 kg/m$^3$), or more preferably, within a range of from about 6 to 12 pcf (96 to 192 kg/m$^3$).

When the body 14 is formed from a cellular material, the cells may be formed either by mechanical incorporation of gases such as air, nitrogen or carbon dioxide into the base polymer under pressure or by the incorporation of a chemical blowing agent, such as one generating $CO_2$, into the polymer material. The chemical blowing agent is then activated, usually by heat, to form a cellular polymer material. The material may in either case be an open or closed cell material.

In a preferred embodiment, the primary ingredients used to fabricate the earplugs of the present invention, i.e., PVC and polymeric plasticizer, are used in substantially similar proportions as used to fabricate conventional die cut earplugs, so as to provide similar degrees of softness and slow, controlled recovery from compression. These properties are important for comfort and ease of insertion in the ear, i.e., to give the user enough time to insert the product into the ear in a compressed state and allow it to expand to create a contoured seal within the ear canal. A useful formulation for fabrication of earplugs 10, 10', 10" of the present invention is as follows:

1. 100 parts by weight of PVC resin. The resin should be of low or medium molecular weight i.e., within a range of 0.55 to 1.1 inherent viscosity (ASTM D1243), with low molecular weight, i.e., 0.85 or less, preferred, because this tends to give a more uniform cell-structure. The particle size and porosity of the resin should be in a range suitable for extrusion of plasticized product (as opposed to plastisol processing or rigid PVC products). A preferred material is OXY 200™, supplied by Oxy Vinyls, L. P. of Dallas, Tex.

2. 60 to 140 parts plasticizer (ADMEX 523™ is one suitable example) to provide the slow recovery from compression. Other plasticizers, such as epoxidized soybean oil, can be blended with the ADMEX 523™ Available from Hüls America of Piscataway, N.J. to increase recovery rate if use of the ADMEX 523™ alone provides a recovery that is too slow.

3. Acrylic processing aid. This material provides melt strength, i.e., it allows the melt to be drawn down to thin membranes during the expansion. A useable range would be about 5 parts to 30 parts.

4. Nucleator. This is particulate material that helps to control cell size. Many types are usable and are effective at 0.1 part up to 20 parts, depending on the type.

5. Stabilizer. This material prevents decomposition of the PVC resin that otherwise may be problematic during processing at elevated temperature. A suitable range is about 0.5 to 10.0 parts.

6. External lubricant. (Optional) This can be a fatty acid, metallic soap, or a wax and its purpose is to prevent the melt from sticking to the hot surfaces inside the extruder. A suitable range is 0 to 5 parts by weight.

7. PVC Dispersion Resin. (Optional) This is to improve powder flow properties without affecting nucleation. A suitable range is 0 to 1 part by weight.

The cross-sectional shape of the body 14 is preferably circular (as shown in FIGS. 1–7), though it may also be otherwise shaped, such as polygonally or irregularly shaped. The preferred cross-sectional diameter B of the body is between about 5 mm and 20 mm, preferably about 10–20 mm.

As mentioned hereinabove, the body 14 preferably includes a continuous skin 18 about its outer surface. This is particularly desirable where the body 14 is formed from a cellular material because the continuous skin 18 protects any open cells along the outer surface from harboring soil. The continuous skin 18 is preferably integrally formed as a result of the extrusion process. However, it can also be provided through chemical or mechanical treatment of the monolithic structure, or it can be provided as an additional layer.

As shown, for example in FIGS. 2 and 4–7, the end portions of the earplugs may have any of a variety of configurations. In particular, it may be desirable to provide earplugs 10 having end portions 16 which are substantially flat or squared-off, such as in FIGS. 2 and 4.

Figure 5:
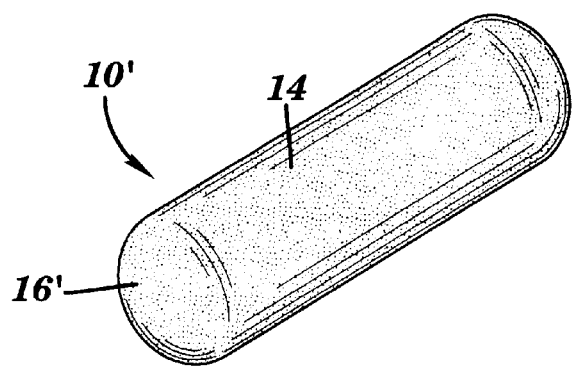
FIG. 5 is a perspective view of an alternate embodiment of the present invention having convex end portions.
Figure 6:
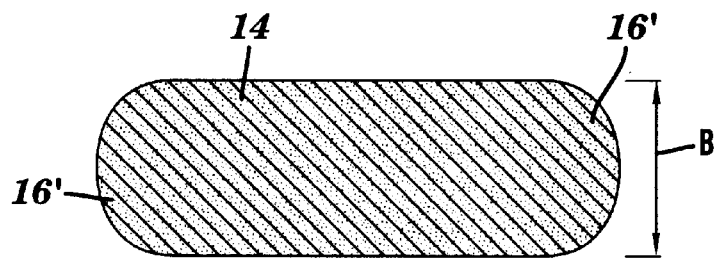
FIG. 6 is a longitudinal cross-sectional view of the earplug shown in FIG. 5.

Alternatively, in a preferred embodiment, generally convex end portions 16' may be provided, as shown in FIGS. 5 and 6. Such a convex configuration may be advantageously attained without any extra operations by using a cutting operation to cut the extrudate substantially immediately upon emerging from the extruder die, as will be discussed in greater detail hereinbelow. Additional geometries, such as the frusto-conical or tapered end portions 16" shown in FIG. 7, may be provided using additional shaping or cutting steps known to those skilled in the art. The convex or tapered end portions 16', 16" generally facilitate insertion thereof into a wearer's ear canals.

The earplugs desirably include two end portions 16 which are of the same shape. However, combinations can be used, such as a conical end portion on one end of the earplug and a convex end portion on the other end of the earplug, so that the wearer may select which shaped end portion is more comfortable in his ear and insert that shaped end portion into his ear.

Figure 9:
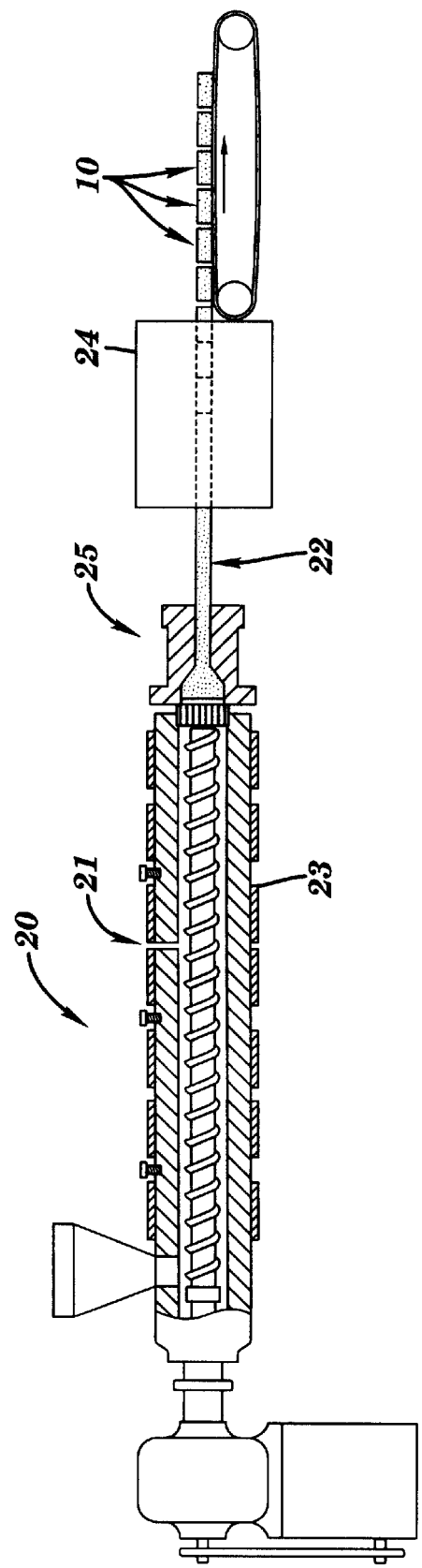
FIG. 9 is a schematic representation of a production apparatus for the earplugs in accordance with the present invention.

The manufacture of the earplugs may be performed with an apparatus as shown in FIG. 9. The body 14 is extruded from an extruder 20 to form a monolithic structure 22. Extruder 20 is substantially similar to those commonly used for making plasticized PVC products, with the exception that an injection nozzle 21 is disposed in the extruder barrel 23 so that the blowing agent may be added to the melted material. An extruder of this type is described in a technical correspondence bulletin published by the Monsanto Company entitled "Extrusion Foaming Technology for Santoprene Thermoplastic Rubber", bulletin number TCD04287. The blowing agent may be a gas or liquefied gas such as $CO_2$. Other gases known to those skilled in the art also may be used. Through the action of heat and pressure, the blowing agent dissolves in the melted material. Upon emerging from the die 25, the release of pressure causes the blowing agent to vaporize or otherwise expand to form the cells of the foam. The monolithic extrudate 22 may then be cut and solidified, with the solidification means being dependent on the material used to form the extrudate. In a preferred embodiment, in which a PVC material is used, the extrudate is cooled in ambient air or by a temperature controlled air bath. Alternately, however, extrudates may be quenched by way of other traditional cooling methods, such as by treating with a liquid or gas bath to cool and solidify the extrudate.

After the monolithic structure 22 emerges from the extruder 20, it is fed to a cutting device 24 (shown schematically) which cuts the extrudate into discrete pieces of the desired length, preferably about 10 to 35 mm, thereby forming individual earplugs. Particularly preferred are earplugs having a length of about 17 to 25 mm. The monolithic structure may be cut into discrete pieces using any of a variety of conventional cutting devices such as a knife blade, hot wire, water jet, or laser, for example. In a preferred embodiment, the extrudate is cut to length in-line using a length cutter (i.e., rotary knife cutter) of the type commonly used in the plastic extrusion industry. Other suitable cutting machines include conventional high speed wire and tubing cutters.

As mentioned hereinabove in a preferred embodiment, it is desired to form earplugs having end portions with convex or otherwise shaped diameters. Such convex end portions 16' may be advantageously formed without any additional process steps by cutting the extrudate at the die face of the extruder as the material emerges therefrom, prior to expansion and cooling thereof. After cutting, the end portions expand and cool, inherently forming a bowed, convex geometry. In addition, a film or skin is formed over the end surfaces as the foam material continues to expand and cool. The earplug thus produced has convex end portions 16' and a film or skin 18 that extends over its entire exterior surface, including both the body 14 and end portions 16'. The skilled artisan will recognize that the exterior surface of body 14 (i.e., the cylindrical surface as shown) of the extrudate will be skinned over as an inherent function of the extruding process. Advantageously, the convex end portions 16' tend to facilitate earplug insertion. Also, this embodiment has been shown to provide better sound attenuation than earplugs having unskinned end surfaces, and is generally less prone to harbor dirt or bacteria. This resistance to dirt also tends to improve the reusability and comfort of the earplugs.

In the alternative, however, rather than cutting the extrudate prior to expansion and cooling, the extrudate may be cut after the expansion and cooling. This will provide an ear plug having squared off ends 16, such as shown and described with respect to FIGS. 2–4.

As also mentioned hereinabove, a further benefit of earplugs 10, 10', and 10" is that the skin 18 on the cylindrical surface thereof increases the longitudinal stiffness of the plug. This tends to facilitate insertion of the extruded plug into the user's ear, relative to prior art die cut plugs.

Figure 7:
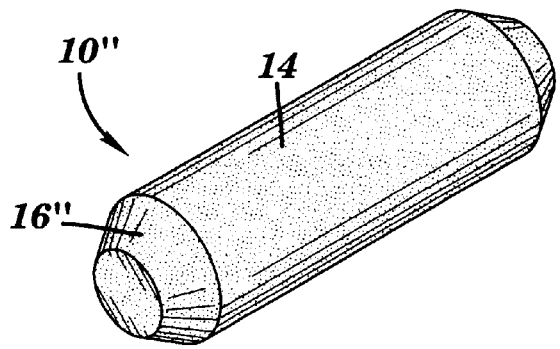
FIG. 7 is a perspective view of an earplug according to an additional embodiment of the present invention having rounded shaped end portions.

In further alternative embodiments as mentioned hereinabove and shown in FIG. 7, end portions 16" may be provided by subjecting the extrudate to additional operations after exiting the die and/or after cooling of the extrudate. For example, the extrudate may be fed to a heated device which compresses and cuts the monolithic body 14. Because the extrudate is heated while it is radially compressed, it retains its compressed configuration following cutting, resulting in end portions of reduced diameter or tapered configuration as shown. The heat can be provided by either directly heating the cutting blades (i.e., when using the above referenced iris-type cutter) or by applying local heat to the tip of the compressed body by a laser or other localized heating device. Alternatively, the extrudate may be compressed prior to complete solidification of the monolithic structure, i.e., while the body 14 is still in a semi-fluid state, to thereby form end portions having reduced diameters.

Still further, the monolithic structure can be compressed in specific regions and cut (in a manner similar to that used to produce sculpted foam pillows) to form sculpted earplug end portions.

Figure 8:
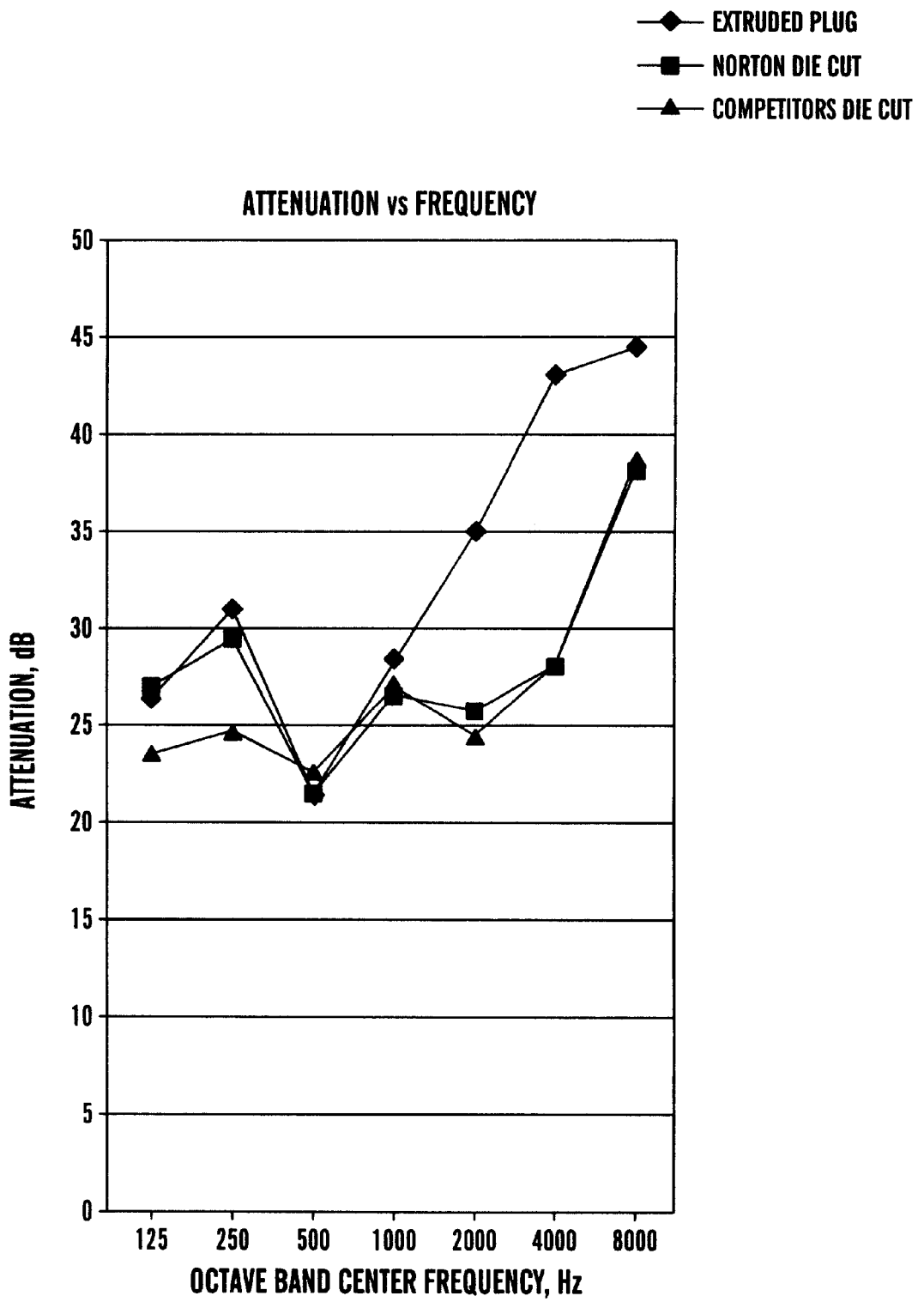
FIG. 8 is a graphical comparison of sound attenuation test results of the earplugs of this invention relative to earplugs of this prior art.

Turning now to FIG. 8, earplugs of the present invention have been tested for sound attenuation relative to conventional die cut earplugs. The (prior art) die cut plugs included the NORTON® SAFG® Earplug manufactured by Norton Company of Worcester, Mass., and the EAR® CLASSIC® manufactured by E-A-R Specialty Composites Corporation of Indianapolis, Ind. As shown, the extruded earplugs of the present invention surprisingly provided substantially improved sound attenuation, especially within the critical 2000 to 8000 Hz range, i.e., the range of frequencies most likely to cause hearing damage.

Still another property difference is the foam densities of the earplugs. The earplugs had densities ranging from 8.9 to 10.7 $lb/ft^3$ (pcf), i.e., (142 to 171 $kg/m^3$), while the die cutplugs had densities of 6.8 and 7.5 pcf (108 to 120 $kg/M^3$), respectively. These different densities are not inherent to the extrusion versus die cast processes, but simply reflected the composition of the specific plugs under test. Moreover, this factor may have actually had a detrimental impact on the sound attenuation of the present invention. Prior earplug testing has indicated that otherwise identical earplugs of higher densities may provide lower sound attenuation than those of lower density.

It is noted that the above-noted production methods generate little, if any, material waste, since the cylindrical shape is generated directly from the die of the extruder and the length is cut-to-finish in-line. Waste is thus substantially eliminated. Moreover, the materials used to fabricate the earplugs 10, 10', 10" is readily recyclable, so that any scrap that is generated, i.e., during start-up of the extruder 20, may be returned to the material supply during subsequent earplug production.

The completed earplugs are desirably provided and packaged in pairs. However, due to the inexpensive and rapid production method taught by the present invention, the earplugs may be provided at a cost sufficiently low for them to be used in a disposable manner whereby they are discarded after a single wearing. However, the resulting earplugs are durable enough that they will withstand repeated wearings by the user.

An additional benefit of the extruded earplugs 10, 10', 10" of the present invention is that, although they may be made in different colors through use of pigments, their natural color is a bright white. This is favorable because the white color connotes cleanliness. Foams commonly used to fabricate die cut plugs generally include plastisol or urethane and are thus naturally tan and difficult to make white, even with pigments.

The following illustrative examples are intended to demonstrate certain aspects of the present invention. It is to be understood that these examples should not be construed as limiting.

EXAMPLES

Example 1

Earplugs are fabricated substantially as shown and described hereinabove with respect to plugs 10 of the present invention. The formulation used to fabricate the plugs is as follows:

| | |
|---|---|
| PVC resin | 95 to 105 parts by weight |
| Plasticizer | 60 to 140 parts by weight |
| Acrylic processing aid | 5 to 30 parts by weight |
| Nucleating agent | .1 to 20 parts by weight |
| Stabilizer | .5 to 10 parts by weight |
| External lubricant (Optional) | 0 to 5 parts by weight |
| Dry flow promoter (Optional) | 0 to 1 part by weight |

Example 2

Earplugs were fabricated substantially as shown and described hereinabove with respect to plugs 10 of the present invention. The formulation used to fabricate the plugs was as follows:

| | |
|---|---|
| OXY 200 ™ PVC resin | 100 parts by weight |
| ADMEX 523 ™ plasticizer | 80 parts by weight |
| Epoxidized soybean oil plasticizer | 7 parts by weight |
| PARALOID K120ND ™ acrylic processing aid | 11 parts by weight |
| OMYACARB 6 ™ calcium carbonate nucleator | 6 parts by weight |
| THERMACHEK 1363 ™ barium zinc stabilizer | 2.5 parts by weight |
| ACRAWAX C ™ external lubricant | 0.5 parts by weight |
| COLORITE CP ™ 1720 PVC resin | 0.25 parts by weight |

The equipment and conditions of this Example were as follows:

Equipment
1. 1 ¾" 32:1 single screw extruder with injection port at the $19^{th}$ turn
2. $CO_2$ and $H_2O$ metering system
3. Static mixers in die zone
4. 0.156" diameter circular exit die
5. Conveying equipment
6. Rotary knife cutter

| Conditions | |
|---|---|
| Barrel Temps (zones 1–4), ° F. | 280, 290, 335, 305 |
| Gate and die temp, ° F. | 288, 225 |
| Screw oil temp, ° F. | 200 |
| Screw speed, rpm | 20 |
| Material throughput, lb/hr | 14.5 |
| % blowing agent | 1.6 |

The resulting earplugs 10 were 0.54 inch (13.7 mm) in diameter and had a density of 8.9 pcf (142.56 kg/m$^3$).

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

Having thus described the invention, what is claimed is:

1. A method of fabricating an earplug, comprising the steps of:
    a) using an extruder having a die to extrude a monolithic body of foamed elastomeric thermoplastic material about 10 to 20 millimeters in diameter; and
    b) at least partially cutting the body into discrete pieces about 10–35 millimeters in length to form individual earplugs;
    wherein the monolithic body has a density within a range of about 2 to 20 pcf (32 to 320 kg/m$^3$).

2. The method of claim 1, wherein said cutting step comprises cutting the body at a 90 degree angle to a longitudinal axis of the body.

3. The method of claim 2, wherein said cutting step is performed after cooling and expansion of the body, to form substantially planar ends on said discrete pieces.

4. The method of claim 2, wherein said cutting step further comprises forming convex end surfaces by cutting the extrudate as it emerges therefrom, prior to substantially complete cooling and expansion, wherein a convex, skinned surface is formed at the ends of the pieces as the extrudate expands and cools.

5. The method of claim 1, further comprising the step of forming a protective skin over the body.

6. The method of claim 5, wherein said cutting step further comprises cutting the body proximate the die face as it emerges therefrom, prior to substantial expansion and cooling thereof, wherein a skin is formed at the ends of the pieces.

7. A monolithic earplug formed by the method of claim 1.

8. The method of claim 1, wherein the monolithic body has a density of about 6 to 12 pcf (96 to 192 kg/m$^3$).

9. A method of fabricating an earplug, comprising the steps of:
a) using an extruder having a die to extrude a monolithic body of foamed elastomeric thermoplastic material about 10 to 20 millimeters in diameter; and
b) at least partially cutting the body into discrete pieces about 10–35 millimeters in length to form individual earplugs;
wherein said monolithic body has a rate of recovery from compression to about 20 percent of its initial volume, and from compression under a 5 pound weight for 6 seconds, sufficient to recover about 90 percent or less of its initial volume in 45 seconds.

10. A method of fabricating an earplug, comprising the steps of:
a) using an extruder having a die to extrude a monolithic body of foamed elastomeric thermoplastic material about 10 to 20 millimeters in diameter; and
b) at least partially cutting the body into discrete pieces about 10–35 millimeters in length to form individual earplugs;
wherein said step of using an extruder further comprises extruding an extrudable material having a rate of recovery from being compressed under a 5 pound weight for 6 seconds, sufficient to recover about 90 percent or more of its initial volume in 90 seconds.

11. A method of fabricating an earplug, comprising the steps of:
a) using an extruder having a die to extrude a monolithic body of foamed elastomeric thermoplastic material about 10 to 20 millimeters in diameter; and
b) at least partially cutting the body into discrete pieces about 10–35 millimeters in length to form individual earplugs;
wherein the elastomeric thermoplastic material includes:
95–105 parts by weight PVC resin;
60 to 140 parts by weight plasticizer;
5 to 30 parts by weight acrylic processing aid;
0.1 to 20 parts by weight nucleator;
0.5 to 10 parts by weight stabilizer;
0 to 5 parts by weight external lubricant; and
0 to 1 part by weight dry flow promoter.

12. The method of claim 11, wherein the thermoplastic elastomeric material comprises:
100 parts by weight PVC resin;
80 parts by weight plasticizer;
7 parts by weight epoxidized soybean oil;
11 parts by weight acrylic processing aid;
6 parts by weight nucleator;
2.5 parts by weight stabilizer;
0.5 parts by weight external lubricant.

13. An earplug sized and shaped for being received in the human ear canal, the earplug comprising:
an extruded monolithic body of foamed elastomeric thermoplastic material about 5 to 20 millimeters in diameter having a length of about 10–35 millimeters;
said earplug having a rate of recovery from 80 percent compression sufficient to recover about 90 percent or less of its initial volume in about 45 seconds.

14. The monolithic earplug of claim 13, having a rate of recovery wherein after being compressed under a 5 pound weight for 6 seconds, the earplug recovers about 90 percent or more of its initial volume in about 90 seconds.

15. A monolithic earplug formed by the process of:
disposing a PVC-based material within an extruder under heat and pressure;
incorporating a blowing agent into the material;
extruding the material in a longitudinal direction from a die into an ambient environment wherein the blowing agent foams the extrudate, the extrudate having a transverse cross-sectional dimension of about 10 to 20 millimeters;
cutting the extrudate at a 90 degree angle to the longitudinal direction as the extrudate emerges from the die and prior to substantially complete cooling and expansion thereof, wherein a convex, skinned surface is formed at the cut ends as the extrudate expands and cools to form a monolithic earplug having a density of about 6 to about 12 pcf (96 to about 192 kg/m$^3$), and a rate of recovery from 80 percent compression sufficient to recover about 90 percent or less of its initial volume in 45 seconds, and after being compressed under a 5 pound weight for 6 seconds, to recover about 90 percent or more of its initial volume in 90 seconds.

16. An earplug sized and shaped for being received in the human ear canal, the earplug comprising:
an extruded monolithic body of foamed elastomeric thermoplastic material about 5 to 20 millimeters in diameter having a length of about 10–35 millimeters;
said earplug having a density between about 2 and 20 pcf (32 to 320 kg/m$^3$).

17. The earplug of claim 16, having a substantially continuous outer skin.

18. The earplug of claim 16, wherein said body has a substantially cylindrical outer surface along at least a majority of its length.

19. The earplug of claim 16, wherein said monolithic body has a cross-sectional diameter of about 10 to 20 millimeters.

20. The earplug of claim 19, wherein said body has a substantially consistent cross-sectional diameter throughout its length.

21. The earplug of claim 16, having a density of between about 6 to 12 pcf (96 to 192 kg/m$^3$).

22. The earplug of claim 16, being formed of a cellular elastomeric thermoplastic material.

23. The earplug of claim 16, further comprising a continuous skin about the outer surface and end portions of said monolithic body.

24. The earplug of claim 23, wherein said end portions are substantially convex.

25. The earplug of claim 23, wherein said continuous skin is formed over said end portions by cutting said body proximate a die face as it emerges therefrom, prior to substantial expansion and cooling thereof, said continuous skin being formed as said thermoplastic material continues to expand and cool.

26. An earplug sized and shaped for being received in the human ear canal, the earplug comprising:
an extruded monolithic body of foamed elastomeric thermoplastic material about 5 to 20 millimeters in diameter having a length of about 10–35 millimeters;
said earplug further comprising a pigment.

* * * * *